(12) United States Patent
Shah

(10) Patent No.: US 11,737,910 B2
(45) Date of Patent: Aug. 29, 2023

(54) SYSTEMS, METHODS, AND DEVICES FOR TREATING MOUTH AND JAW DISORDERS

(71) Applicant: Mamta Ketan Shah, Fremont, CA (US)

(72) Inventor: Mamta Ketan Shah, Fremont, CA (US)

( * ) Notice: Subject to any disclaimer, the term of this patent is extended or adjusted under 35 U.S.C. 154(b) by 711 days.

(21) Appl. No.: 16/137,335

(22) Filed: Sep. 20, 2018

(65) Prior Publication Data

US 2019/0091060 A1 Mar. 28, 2019

Related U.S. Application Data

(60) Provisional application No. 62/562,198, filed on Sep. 22, 2017.

(51) Int. Cl.
*A61F 5/56* (2006.01)
*A63B 23/03* (2006.01)
(Continued)

(52) U.S. Cl.
CPC ............... *A61F 5/566* (2013.01); *A61C 7/08* (2013.01); *A63B 23/032* (2013.01); *A61C 7/282* (2013.01);
(Continued)

(58) Field of Classification Search
CPC ...... A61F 5/566; A61F 5/56; A61F 2005/563; A61F 5/58; A61F 5/0006; A61F 5/00; A61C 7/08; A61C 19/063; A61C 9/0006; A61C 6/00; A61C 7/00; A61C 19/06; A61C 19/08; A61C 17/10; A61C 5/90; A61C 7/36; A61C 7/282; A61C 9/00; A63B 23/18; A63B 71/085; A63B 23/032; A63B 71/08; A63B 71/081; A63B 2071/086; A63B 2071/088; A61M 16/0488; A61M 16/049; A61M 16/0493; A61M 16/0495;
(Continued)

(56) References Cited

U.S. PATENT DOCUMENTS 2,311,158 A 2/1943 Conway et al.
2,776,486 A * 1/1957 Manczur .............. A61C 9/0006
433/35
(Continued)

FOREIGN PATENT DOCUMENTS

DE 20 2009 011 964 U1 2/2011
JP 2013-106811 6/2013
(Continued)

OTHER PUBLICATIONS

Merriam-Webster, "fiber," https://www.merriam-webster.com/dictionary/fiber.*

(Continued)

*Primary Examiner* — Victoria Hicks Fisher
(74) *Attorney, Agent, or Firm* — Knobbe, Martens, Olson & Bear LLP

(57) ABSTRACT

Maxillary and mandibular appliances can be mounted to a user's upper and lower jaws. The appliances can include a palatal pad, buccal tubes, hamular notch tubes, and an anterior deprogrammer. The various portions of the appliances can provoke beneficial reactions by muscles in the tongue and jaw area, massage the same muscles, or provide other beneficial effects.

21 Claims, 10 Drawing Sheets

(51) Int. Cl.
| | |
|---|---|
| *A61C 7/08* | (2006.01) |
| *A63B 71/08* | (2006.01) |
| *A61C 7/28* | (2006.01) |
| *A61C 7/36* | (2006.01) |

(52) U.S. Cl.
CPC ........... *A61C 7/36* (2013.01); *A61F 2005/563* (2013.01); *A63B 71/085* (2013.01)

(58) Field of Classification Search
CPC .. A61B 13/00; A61B 17/24; A61J 7/00; A61J 7/0069; A61J 7/0092
USPC ................................................. 128/859, 848
See application file for complete search history.

(56) References Cited

U.S. PATENT DOCUMENTS

| | | | | |
|---|---|---|---|---|
| 3,818,906 | A * | 6/1974 | Stubbs .................... | A61B 1/24 606/234 |
| 9,375,289 | B1 * | 6/2016 | Walls ....................... | A61C 7/08 |
| 2004/0005525 | A1 | 1/2004 | Brattesani | |
| 2004/0045556 | A1 | 3/2004 | Nelson et al. | |
| 2010/0043804 | A1 * | 2/2010 | Razmovski ............. | A61F 5/566 128/848 |
| 2011/0220125 | A1 | 9/2011 | Van Dyke et al. | |
| 2013/0087157 | A1 * | 4/2013 | Hawkins .............. | A63B 71/085 128/859 |
| 2014/0227657 | A1 * | 8/2014 | Sanders ................... | A61C 5/90 433/32 |
| 2017/0020716 | A1 * | 1/2017 | Hart ...................... | A63B 71/085 |
| 2018/0078337 | A1 * | 3/2018 | Way ........................ | A61K 35/32 |
| 2018/0344507 | A1 * | 12/2018 | Alglave .................. | A61F 5/566 |

FOREIGN PATENT DOCUMENTS

| | | |
|---|---|---|
| WO | WO 2012/155214 A1 | 11/2012 |
| WO | WO 2014/017645 A1 | 1/2014 |
| WO | WO 2017/020079 A1 | 2/2017 |

OTHER PUBLICATIONS

M. Abate et al., "Cigarette smoking and musculoskeletal disorders," 2013, Muscles, Ligaments and Tendons Journal, 3 (2): 63-69 (Year: 2013).*
Merriam-Webster, "treatment," https://www.merriam-webster.com/dictionary/treatment.*
International Preliminary Report on Patentability in International Application No. PCT/US2018/052067, dated Jan. 10, 2020.
Baad-Hansen, L., "Effect of a nociceptive trigeminal inhibitory splint on electromyographic activity in jaw closing muscles during sleep," J Oral Rehabil, Feb. 2007, vol. 34, No. 2, pp. 105-111.
Bronson, J., "Introducing the Advanced Light Force(ALF) Appliance," Oral Health, https://www.oralhealthgroup.com/features/introducing-the-advanced-light-force-alf-appliance/, published Mar. 1, 2015, accessed Feb. 26, 2019, 10 sheets.
Broomes, G., "Tensegrity in Biology," The Fascia Therapy Blog, https://thescienceofphysicalrehabilitation.blogspot.com/2012/07/tensegrity-in-biology.html, published Jul. 15, 2012, accessed Feb. 26, 2019, 13 sheets.
Burgan, B., "How Does Massage Work?", https://www.takingcharge.csh.umn.edu/explore-healing-practices/massage-therapy/how-does-massage-work, accessed Feb. 19, 2019, 3 pages.
Buscà, B. et al., "Effects of jaw clenching wearing customized mouthguards on agility, power and vertical jump in male high-standard basketball players," Journal of Exercise Science & Fitness, 2018, vol. 16, pp. 5-11.
Buscà, B. et al., "Effects of Jaw Clenching While Wearing a Customized Bite-Aligning Mouthpiece on Strength in Healthy Young Men," Journal of Strength and Conditioning Research, 2016, vol. 30, No. 4, pp. 1102-1110.
Cai, M. et al., "Effect of head and jaw position on respiratory-related motion of the Genioglossus," J. Appl. Physiol., 2016, vol. 120, pp. 758-765.
Camacho, M. et al., "Myofunctional Therapy to Treat Obstructive Sleep Apnea: A Systematic Review and Meta-analysis," Sleep, 2015, vol. 38, No. 5, pp. 669-675.
ChairsideSplint.com, website http://chairsidesplint.com/, accessed Feb. 25, 2019, 1 sheet.
"Chapter 51: The mouth tongue and teeth," Basic Human Anatomy—O'Rahilly, Muller, Carpenter & Swenson, 2008, https://www.dartmouth.edu/~humananatomy/part_8/chapter_51.html#chpt_51_legends, Dartmouth Medical School, accessed Feb. 25, 2019, 6 sheets.
Cheng, S. et al., "Movement of the tongue during normal breathing in awake healthy humans," The Journal of Physiology, Sep. 1, 2008, vol. 586 (Part 17), pp. 4283-4294.
Clark, G., Classification, Causation and Treatment of Masticatory Myogenous Pain and Dysfunction, Oral and Maxillofacial Surgery Clinics of North America, May 2008, vol. 20, Issue 2, pp. 145-157.
Cunha, John P., "Temporomandibular Joint Syndrome (TMJ)," MedicineNet, https://www.medicinenet.com/temporomandibular_joint_syndrome_tmj/article.htm#emporomandibular_joint_tmj_syndrome_facts, dated Jan. 22, 2018, accessed Feb. 26, 2019, 8 sheets.
Di Vico, R. et al., "The acute effect of the tongue position in the mouth on knee isokinetic test performance: a highly surprising pilot study," Muscles Ligaments Tendons Journal, Oct.-Dec. 2013, vol. 3, No. 4, pp. 318-323.
Edwards, B. et al,. "Control of the Pharyngeal Musculature During Wakefulness and Sleep: Implications in Normal Controls and Sleep Apnea," Head Neck, Oct. 2011, vol. 33 (Suppl. 1), pp. S37-S45.
Fonder, Dr. Aelred C., "The Dental Distress Syndrome Quantified," The Best of Basal Facts—V9, pp. 1205-1233, http://www.icnr.com/articles/dental-distress-syndrome-quantified.pdf, accessed Feb. 14, 2019.
Greene, C., "The Etiology of Temporomandibular Disorders: Implications for Treatment," Journal of orofacial pain, Feb. 2001, vol. 15, No. 2, pp. 93-116.
Ieto, V. et al., "Effects of Oropharyngeal Exercises on Snoring: A Randomized Trial," Chest, Sep. 2015, vol. 148, Issue 3, pp. 683-691.
Kreucher, B., "Tip of the Tongue / Roof of the Mouth," Living in Harmony, http://realdoctor.blogspot.com/2006/09/tip-of-tongue-roof-of-mouth.html, accessed Feb. 26, 2019, 2 sheets.
International Search Report and Written Opinion dated Apr. 3, 2019 in International Application No. PCT/US2018/052067, 21 pages.
Kuhn, M. et al,. "Risk factors for bruxism," Swiss Dental Journal SSO, 2018, vol. 128, pp. 118-124.
Kwan, Benjamin C.H. et al., "Influence of respiratory mechanics and drive on genioglossus movement under ultrasound imaging," PLoS ONE, 2018, vol. 13, No. 4, 19 pages.
Liu, Z.L. et al., "Effects of tongue volume reduction on craniofacial growth: A longitudinal study on orofacial skeletons and dental arches," Arch Oral Biol., Oct. 2008, vol. 53, No. 10, pp. 991-1001.
Lopez, Daniel D.O., "How Swallowing Incorrectly can Affect Your Eyes," https://www.daniellopezdo.com/swallowing-incorrectly-can-affect-eyes/, dated Jul. 3, 2017, accessed Feb. 25, 2019, 6 sheets.
Massey, B., "Physiology of oral cavity, pharynx and upper esophageal sphincter," GI Motility online, https://www.nature.com/gimo/contents/pt1/full/gimo2.html, doi:10.1038/gimo2, 2006, Published May 16, 2006, accessed Feb. 26, 2019, 13 sheets.
Maurer, C. et al., "Influence of the Lower Jaw Position on the Running Pattern," PLoS ONE, 2015, vol. 10, No. 8, 16 pages.
Maurer, C. et al., "Strength improvements through occlusal splints? The effects of different lower jaw positions on maximal isometric force production and performance in different jumping types," PLoS ONE, 2018, vol. 13, No. 2, 17 pages.
Mercola, Dr. J., "Oral Myofacial Therapy—A Breakthrough Technique to Treat Symptoms Relating to Breathing Problems, TMJ, Headaches and Other Common Ailments," https://articles.mercola.com/sites/articles/archive/2013/04/07/orofacial-myofunctional-therapy.aspx, dated Apr. 7, 2013, accessed Feb. 19, 2019, 9 pages.

(56) References Cited

OTHER PUBLICATIONS

Messina, G., "The Tongue, Mandible, Hyoid System," Eur J Transl Myol, 2017, vol. 27, No. 1, pp. 74-76.
Mew, Dr. M., "Should Tongue Rest/Touch at the Palate/ Maxilla/ Roof of the Mouth By Dr Mike Mew," https://www.youtube.com/watch?v=eh9OqEd5z1k (full video available on website), dated Mar. 19, 2015, accessed Feb. 19, 2019, 2 sheets.
Muscular hydrostat, from Wikipedia, https://en.wikipedia.org/wili/Muscular-hydrostat, accessed Feb. 19, 2019, 5 pages.
Myers, T., "Fascia lines for treatment: A look at Anatomy Trains by Tom Myers," Atlasbalans, https://www.atlasbaians.com/fascial/fascia-lines/, 2018, accessed Feb. 26, 2019, 16 sheets.
Ohlendorf, D. et al., "The significance of lower jaw position in relation to postural stability. Comparison of a premanufactured occlusal splint with the Dental Power Splint," Minerva Stomatol, Nov.-Dec. 2013, vol. 62, Nos. 11-12, pp. 409-417.
Partial International Search Report dated Jan. 30, 2019, issued in International Application No. PCT/US2018/052067, 13 pages.
Prigg, M., "Study reveals six tongue exercises that can Cure snoring," https://www.dailymail.co.uk/sciencetech/article-3072739/The-tongue-excercises-CURE-snoring-Researchers-reveal-six-simple-steps-better-sleep.html, Dailymail.com, updated May 8, 2015, accessed Feb. 19, 2019, 5 pages.
Rogers, J. et al., "The Controversy of Cranial Bone Motion," Journal of Orthopedic & Sports Physical Therapy, Aug. 1997, vol. 26, No. 2, pp. 95-103.
Rugh, J.D. et al., "Nocturnal bruxism and temporomandibular disorders," Adv. Neurol., 1988, vol. 49, pp. 329-341.
Rugh, J.D. et al., "Psychological implications in temporomandibular pain and dysfunction," Oral Sciences Reviews, Jan. 1, 1976, vol. 7, pp. 3-30.
Sanders, A.E. et al., "Sleep Apnea Symptoms and Risk of Temporomandibular Disorder," Journal of Dental Research, Jul. 2013, vol. 97 (7 Suppl.), pp. S70-S77.
Sanders, I. et al., "A 3-Dimensional Atlas of Human Tongue Muscles," Anat Rec (Hoboken), Jul. 2013, vol. 296, No. 7, pp. 1102-1114, 20 pages.
Sanvito, Alice, "Pushing Into Muscle: Are We Really Doing What We Think We Are Doing?"; http://www.massage-stiouis.com/blog/pushing-muscle-are-we-really-doing-what-we-think-we-are-doing; dated May 14, 2012; accessed Feb. 14, 2019.
Scarr, G., "Examining the Temporo-Mandibular Joint From a Biotensegrity Perspective: A Change in Thinking," Journal of Applied Biomedicine, Jan. 2017, vol. 15, Issue 1, pp. 55-62.
Schuyler, C., "The Function and Importance of Incisal Guidance in Oral Rehabilitation," The Journal of Prosthetic Dentistry, Nov.-Dec. 1963, vol. 13, Issue 6, pp. 1011-1029 (1 sheet, p. 1011).
Sforza, C. et al., "Occlusion, Sternocleidomastoid Muscle Activity, and Body Sway: A Pilot Study in Male Astronauts," The Journal of Craniomandibular & Sleep Practice, Jan. 2006, vol. 24, Issue 1, pp. 43-49.
Shetty, S. et al., "Bruxism: A Literature Review," J. Indian Prosthodont Soc., Jul.-Sep. 2010, vol. 10, No. 3, pp. 141-148.
Stanchina, ML et al., "The influence of lung volume on pharyngeal mechanics, collapsibility, and genioglossus muscle activation during sleep," Sleep, Nov. 1, 2003, vol. 26, No. 7, pp. 851-856.
Stapelmann, H. et al., "The NTI-tss device for the therapy of bruxism, temporomandibular disorders, and headache—Where do we stand? A qualitative systematic review of the literature," http://www.biomedcentral.com/1472-6831/8/22, BMC Oral Health, 2008, vol. 8, No. 22, 23 pages.
Stone, M. et al., "Structure and variability in human tongue muscle anatomy," Comput Methods Biomech Biomed Eng Imaging Vis., 2018, vol. 6, No. 5, pp. 499-507, 20 pages.
Straub, W., "Malfunction of the tongue," AJO-DO: American Journal of Orthodontics & Dentofacial Orthopedics, Jun. 1960, vol. 46, Issue 6, pp. 404-424.
Sugawara, Y. et al., "Orthodontic treatment of a patient with unilateral orofacial muscle dysfunction: The efficacy of myofunctional therapy on the treatment outcome," AJO-DO: American Journal of Orthodontics & Dentofacial Orthopedics, Jul. 2016, vol. 150, Issue 1, pp. 167-180.
Thompson, B.A. et al., "Treatment approaches to bruxism," Am Fam Physician, May 15, 1994, vol. 49, No. 7, pp. 1617-1622.
Wanveer, T., "The Tongue: How Craniosacral Therapy Can Help This Important Muscle," https://www.massagemag.com/the-tongue-how-cranioscaral-therapy-can-help-this-important-muscle-6274/, dated Oct. 20, 2009, accessed Feb. 19, 2019, 4 pages.
Weerapong, P. et al., "The Mechanisms of Massage and Effects on Performance, Muscle Recovery and Injury Prevention," Sports Medicine, Mar. 2005, vol. 35, Issue 3, pp. 235-256.
Wright, E.F. et al., "Management and treatment of temporomandibular disorders: a clinical perspective," J. Man Manip Ther., 2009, vol. 17, No. 4, pp. 247-254.
Yap, A. et al., "Sleep bruxism: Current knowledge and contemporary management," J. Conserv Dent., Sept.-Oct. 2016, vol. 19, No. 5, pp. 383-389.
Zaghi, Soroush, "Lecture #1: Introduction to ankyloglossia and UARS (AAMS Congress, Mar. 2017)," https://www.youtube.com/watch?v=d7b_ap/ASv2I&app=desktop (full video available on website), dated May 2, 2017, accessed Feb. 19, 2019, 3 sheets.

* cited by examiner

SYSTEMS, METHODS, AND DEVICES FOR TREATING MOUTH AND JAW DISORDERS

BACKGROUND

Field

The application relates to systems, methods, and devices for treating various musculoskeletal disorders and issues in the mouth and jaw joints.

Description of the Related Art

The present invention can relate to clinical protocols, devices, systems, and treatment methods directed at temporarily aligning the musculature thus helping to correct orofacial pain, temporomandibular joint ("TMJ") dysfunction, sleep-related breathing disorders and variations of aberrant osteopathic movements of the cranium and aberrant tongue position and swallow pattern, allowing a function correction (a treatment that changes soft tissues and soft tissue spaces), and aiding in foundational correction (a treatment that changes the skeletal and/or dental issues).

Temporo-mandibular disorder ("TMD") is a musculoskeletal disorder within the masticatory system, often viewed as a repetitive motion disorder of the same. It is a very common problem affecting up to 33% of the American population within their lifetime with pain persisting 6 months or longer.

Localized TMJ pain may be spontaneous or triggered in the masseter muscle, preauricular area, temporalis muscle, and/or the supra and infra hyoid region. Often, pain may be mild to moderate with or without pressure or burning sensations. 3-7% of these patients have TMD related pain, sharp and throbbing, intensified by stress and clenching, and severe enough to cause them to seek treatment. Other sub-diagnoses could be myofascial pain, temporomandibular inflammation etcetera. As with other musculoskeletal disorders, pain during function and at rest is the primary reason patients seek treatment, and a reduction in pain is generally the primary goal of therapy. Less commonly, individuals seek TMD therapy for TMJ locking or popping, masticatory muscle stiffness, limited mandibular range of motion, TMJ dislocation, unexplained change in occlusion (anterior or posterior open bite), or shift in the mandibular midline.

Usual TMD self-management instructions to patients are to limit masticatory muscle activity by limiting use of the mouth, for example: avoid hard sticky chewy foods, yawning with mouth wide open, and consciously restricting parafunctional activity like clenching and grinding.

However, TMD and discomfort and pain associated with it are not limited to the joint itself.

There appears to exist a controlling relationship within the body that puts the dental system into a causative role of symptomatology, where a dysfunctioning dental occlusion creates ill effects throughout many distant areas of the united body. Dr. Fonder has termed this the Dental Distress Syndrome.

The apex of the combined muscular control of the mandible in all functioning movements is located at the center of the dens between the Atlas (C1) and Axis (C2) cervical vertebrae. When the mouth opens, the 136 muscles above and below the mandible pivot the jaw at the axis connecting the incisal edge of the upper central incisor to the center of dens according to Casey Guzay's 'The Quadrant Theorem'. Therefore, mandibular muscle dysfunction affects posturing of C1 and C2.

Maintaining the ideal and congruent position of C1 and C2 is the most important in maintaining spinal curvatures according to Dr. Mariano Rocabado.

According to Dr. Fonder and other researchers, the malpositioning of C1 and C2 and the resultant mandibular dysfunction torques the duramater because of the frontal and dorsal attachment it has to C1, C2, and C3.

Torquing the duramater causes scoliosis, cervical hypolordosis, thoracic hyperkyphosis, excessive lumbar lordosis, rotation of the pelvis causing uneven leg length and shoulder height, etcetera.

Dr. Fonder says, we swallow twice a minute when awake and once a minute when asleep. If we subject the teeth to only one pound of pressure per square inch with each act of swallowing, the dental structures would absorb approximately one ton of intermittent pressure daily. However, the average person exerts at least three and one half pounds of pressure during swallowing and bruxers far exceed this norm. Hence, stressful musculoskeletal disorders result in many tons of intermittent dental stress in erroneous feedback that constantly upsets the balance of the body's systems.

SUMMARY

We have found that when the 136 muscles of head, face and neck are allowed to assume a more physiologically balanced relationship to each other in rest and in function, the head uprights, pelvic rotation corrects, and overall body posture normalizes.

The tongue being the antagonist to the closing muscles of the mouth, this correction can only happen if the tongue compresses against the roof of the mouth, thus maintaining biotensegrity to manage the interplay between force, tension, and function in the craniomandibular system hence allowing functional harmony between the supra and infrahyoid muscles and the muscles anterior and posterior to the dens of C2. Nocturnal bruxism may be an attempt by the patient's subconscious to protect the airway during sleep. Patency of the airway is maintained by middle and inferior pharyngeal constrictor muscles attached to the hyoid bone and mandibular symphysis on one end and C3 on the other. When these muscles contract, it brings the symphysis closer to the cervical spine, closing the airway. Hence normal length of these muscles can help maintain airway patency. By encouraging the entire tongue, not just the tip of it, to stay to the roof of the mouth and maintaining its tonicity, the normal length of the pharyngeal muscles is maintained thus sustainably maintaining airway patency during sleep.

The devices and methods disclosed in the present application can be applied in a variety of situations, such as:
1. Relief of pain from TMJ dysfunction
2. Relief of snoring and sleep related breathing disorders and sleep apnea
3. Myofunctional training aid or as an adjunct to treatment protocol by myofunctional therapists.
4. Short term Cleft palate obturator
5. Aid the dentist in finding the most harmonized and bilaterally balanced position of the mandible when treating TMJ and sleep disorders and while making a bite registration for a TMJ or sleep appliance.
6. Encourages nasal breathing by allowing the tongue to push against the palate and opening the naso-pharynx and oro-pharynx.
7. Cranial Osteopaths can use this appliance before and after manipulations to help relieve sutural tensions and hold treatment changes.

8. Chiropractors can use this appliance before and after their treatment to ease the muscles thus improving the congruency of the vertebrae of the cervical spine and subsequently the rest of the vertebral column and hold their treatment changes because the appliance positively balances and harmonizes the musculature of the head, face and neck.

9. Temporary relief of tinnitus

10. As an adjunct to ongoing orthodontic treatment to modify facial growth or as a guard that can be worn to continuously maintain joint congruency as the teeth are moved.

11. ENT surgeons and dentists can use the devices after maxillary and/or mandibular frenectomy to aid in proper healing.

12. Can be used as a sports guard for certain sports.

13. Can be used as a temporary or alternative treatment for patients with movement disorders that are linked to TMJ dysfunction with few or no undesirable side effects (such as facial dystonias and Tourette's syndrome).

14. Can be used as a night guard or mouth guard for clenching and nocturnal bruxism and to protect jaw joints.

15. Can be used as an oral appliance for patients with neurological and/or neuropsychiatric disorders.

16. Can be used to improve athletic performance like a PPM mouth guard.

17. These devices can be worn even if there are no teeth. Most appliances take support from the teeth.

18. Can be used as a relief for headaches, vertigo and balance issues.

19. Can be used as a device to improve strength, balance and flexibility without having to use any sophisticated measuring devices like tensing units. Can be used in patients that have a pacemaker, seizure patients, or pregnant mothers.

20. As a guard to protect extensive dental work and full mouth rehabilitation.

21. As a guard to protect the soft tissues and also to isolate those tissues while the dentist is working in the patient's mouth.

22. As a device for delivering medications

23. As a device to address imbalances of the neutral zone

The devices described herein can be fluid-filled, gel-filled, fiber filled, or medicament filled, or can be solid made out of a single durometer hardness or multiple hardnesses in the same device. They can be injection molded, blow molded, 3D-printed, rotomolded, or formed from any manufacturing method that is available now or will be in the future. They can also be made with micro motors to incorporate healing frequencies such as a "cat purr" frequency (for example, between 25 and 150 Hz) or any other healing frequencies.

One embodiment of the invention consists of a non-rigid fluid filled manufactured maxillary appliance made of interconnecting tubes and bulges that are placed in the maxillary vestibule, hamular notch and palate. The force on the appliance comes from the tongue resting/pushing against the palatal component. This is necessary to maintain the tension and compression necessary to establish normal function of the musculature in a dysfunctional craniomandibular system anterior and posterior to the dens of C2 and the muscles superior and inferior to the hyoid bone.

Another embodiment consists of a manufactured mandibular non-rigid fluid filled appliance of interconnecting tubes and pads that are placed in the buccal vestibule and arms that lie on the floor of the mouth.

Another embodiment of the appliance is decreasing the flexibility of the appliance by increasing the amount of fluid filled if more rigidity is required, for example, to encourage maxillary expansion or to help train for isometric muscle contraction exercises. Another embodiment of the appliance consists of either gel filled, fiber filled or a solid appliance made of a single durometer hardness of the material or various hardnesses in the same device. For example, the deprogrammer can be made harder than the tubes. Material choices can also be different in the same device for different parts. The deprogrammer can be incorporated in the upper device or the lower device. The tubes and pads can be different thicknesses (thicker or thinner). In another embodiment, the deprogrammer can be made semi-adjustable by adding a pivoting hinge on the base of the pad between the pad and the shank connecting the deprogrammer pad to the shank. This hinge can be made such that it tilts 360 degrees to make it parallel to the hamular notch incisive papilla plane ("HIP") and/or to accommodate for the 'cant' of the maxilla left-to-right. The deprogrammer can be made semi-customizable (i.e. of variable thickness) by attaching or detaching, one-half to one millimeter sheets of material as needed by patients to make it such that the thickness of the deprogrammer is just enough to disclude the posterior teeth. Another embodiment can have pads added to the chewing surfaces of the teeth if needed. Another embodiment can have a flange added to the upper or lower device so as to be made usable as a sports guard for contact sports.

The appliance can also incorporate a heating element in one or several locations providing moist heat intraorally to relieve overloaded opening and closing muscles of the mandible. The appliance can also have microsensors to monitor muscle activity and/or for biofeedback therapy.

These are manufactured devices that can reach out to many more people suffering from the above mentioned dental issues and thus can be a very affordable alternative to customized oral orthotics.

In an embodiment, a maxillary appliance configured to be mounted to a user's upper jaw can include a palatal pad, two hamular notch tubes, and two buccal tubes. The palatal pad can be configured to be mounted beneath a palate when mounted to the user's upper jaw. The two hamular notch tubes can be connected to the palatal pad and be configured to mount around a maxillary tuberosity and sit in the hamular notch when mounted to the user's upper jaw. The two buccal tubes can extend between the two hamular notch tubes along opposite upper and middle buccinators when mounted to the user's upper jaw.

In a further embodiment, a maxillary appliance configured to be mounted to a user's upper jaw can include a palatal pad, an anterior deprogrammer, and two buccal tubes. The palatal pad can be configured to be mounted beneath a palate when mounted to the user's upper jaw. The anterior deprogrammer can be connected to the palatal pad and be configured to cover a biting portion of one or more lower incisors when mounted to the user's upper jaw. The two buccal tubes can extend from the anterior deprogrammer along opposite upper and middle buccinators when mounted to the user's upper jaw.

In a further embodiment, a mandibular appliance configured to mount to a user's lower jaw and teeth can include two buccal tubes and an anterior deprogrammer. The two buccal tubes can extend from a central anterior portion of the user's lower jaw rearwardly along opposite mandibular buccinators when mounted to the user's lower jaw. The anterior deprogrammer can be connected to the two buccal tubes and be configured to cover a biting portion of one or more lower incisors when mounted to the user's lower teeth.

In a further embodiment, a system for treating musculoskeletal disorders and issues in the mouth and jaw joints can include the maxillary and mandibular appliances described herein, such that the appliances can be mounted simultaneously in the user's upper and lower jaws. Similarly, methods can be provided where the appliances described herein can be mounted to the user's upper jaw and/or lower jaw.

BRIEF DESCRIPTION OF THE DRAWINGS

Further objects, features and advantages will become apparent from the following detailed description taken in conjunction with the accompanying figures showing illustrative embodiments, in which.

DETAILED DESCRIPTION

Figure 1:
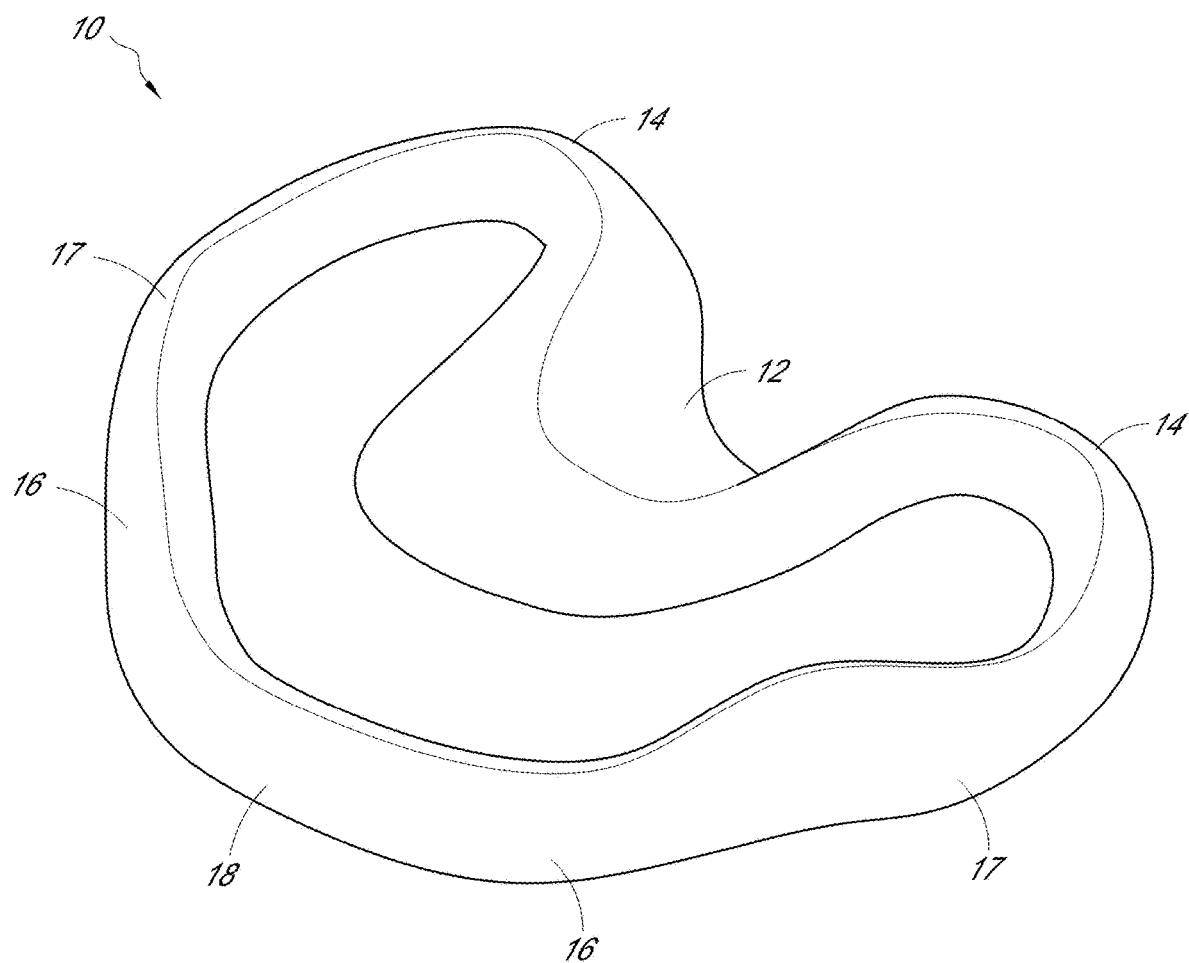
FIG. 1 is a perspective view of an embodiment maxillary appliance.

The maxillary devices depicted in the figures give the anterior, middle and posterior parts of the tongue a reference (a false palate), for retraining muscles and deprogramming them, thus maintaining tongue position while it is worn. The buccal pads (depicted as bulges) and tubes address the imbalances in the upper and middle bands of the buccinators-orbicularis oris complex. The pressure applied to the false palate and the buccal vestibule created by the appliance, through a provoked upward motion of the tongue and perioral musculature by the buccal tubes and bulges, and the relaxation of lateral pterygoid caused by the hamular notch tube, has the potential to synchronize the activity of the 136 muscles of the head, face, and neck. The hamular notch tube can seat the mandibular condyles in centric relation by keeping the lateral pterygoid muscles relaxed. The buccal pad (or bulge) is designed to address the insertion of the upper and middle bands of the buccinator muscles. There will be a massaging of the muscles directly for some of these muscles and indirectly for others. This contact and massaging promotes a relaxation response and mechanical response like in massage therapy while maintaining the tonicity of the muscles of the tongue and airway in wakefulness and in sleep whenever the appliance is worn and can subsequently become a habitual tongue position over time once the muscles are trained.

The mandibular appliance allows the anterior, middle, and posterior part of the tongue to be lifted up when it lacks the muscle tone to stay up to the roof of the mouth. The anterior deprogrammer releases the elevator muscles. The anterior deprogrammer separates the posterior teeth so deflective posterior interferences cannot influence the musculature to displace the condyles. The buccal pad (or bulge) on the mandibular appliance addresses the insertion of the lower band of the buccinators muscles. The mandibular appliances can address all the above issues of muscle disharmony.

Appliances described herein have the potential to place all the muscles of the stomatognathic system in a craniomandibular and craniocervical neutral position. Release of myofascial tension reduces muscle inflammation and increases the rate of muscle repair. Appliances described herein can reduce painful muscle spasms and nerve compression. The maxillary and mandibular appliances can be worn simultaneously or independently. Further, the appliances can optionally be worn for extended periods of time such as during sleep or during the day.

Current art appliances focus on moving teeth. They do not address the underlying cause of poor musculoskeletal homeostasis. Disharmony of muscles causes displacement and disproportional development of bones in a growing child and musculoskeletal pain and sleep disorders in adults. Using the appliances disclosed herein allows autocorrecting the soft tissues and muscles of the head, face, and neck, by using the tongue, which is a very powerful central muscle in the body, as a scaffold which is mimicking nature and will tend to readjust and realign the compensatory mechanisms thus addressing the dysfunction by changing the oral environment and promoting normal growth and development. Appliances described herein can help reinforce and maintain the tongue in a new neutral position and by allowing the tongue to maintain the position, tone, and strength it can support the newly acquired normal physiologic position and functional patterns. This aids the mandible to come to its physiologic rest position. Allowing the muscles to function in their physiologic state reduces the sympathetic tone and increases the parasympathetic nervous system activity thus reducing the flight-or-fight response of the body.

Current TMD, orthodontic, and sleep treatment modalities use positions and forces provided by the treating provider and are thus subject to providers' abilities and inadequacies. Appliances described herein can use the body's innate ability to naturally achieve homeostatic balance in all 3 dimensions encouraging a normal swallow without unusual and excessive muscle tension of all muscles involved. The body's self-regulating muscle balancer optimizes the biomechanics of the body.

Most prior art appliances are rigid or semi-rigid and place the mandible in a forward position. They hence lack the potential to overstretch the muscles, especially lateral pterygoids, for long periods of time thus, causing muscle fatigue. This may actually create a dysfunction by displacing the articular disc of the TMJ or potentiate one if it exists. Overstretching the muscles may cause ligament hypermobility and laxity and may cause the TMJ to function beyond its normal physiologic range of 70% thus causing permanent damage. The disclosed appliances can be non-rigid hydrodynamic fluid filled appliances intended to reduce or remove dysfunctional states by achieving a neuromuscular balance of all muscles of stomatognathic system in a craniocervical and craniomandibular neutral position, thus achieving relief of symptoms in patients with TMJ dysfunction.

The appliances can be used a temporary relief for migraine and other types of headaches. Parafunction is modulated by the trigeminal nerve. Relief of headaches can be achieved if nociceptive input from the trigeminal nerve because of an overloaded muscle can be reduced. The anterior deprogrammer of the appliance can effectively reduce the nociceptive input because it shuts-off the elevator muscles very quickly once the appliance is worn.

The disclosed appliances can also be adapted for and used in patients without teeth unlike the prior art appliances that need teeth to keep them in place and are thus non usable by edentulous patients. Prior art appliances snap on to the teeth and cover the teeth for long periods of time potentially allowing accumulation of plaque and calculus and possibly causing gum disease and tooth decay. Certain features described herein allow the appliances to not take support from teeth. Further the appliances can be easily removed for cleaning of both the appliances and the mouth.

Further, since the disclosed appliances need not be disposed between the molar teeth it helps rapidly alleviate the pain coming from the elevator muscles. Placing something between the teeth triggers a natural reflex to chew, which can thus prevent relaxation of the muscles. When the tongue is in its physiologic resting position to the roof of the mouth, posterior teeth are naturally slightly discluded. Posterior disclusion reduces the elevating activity of the temporal, masseter, medial pterygoid, and superior belly of the lateral pterygoid muscles. Hence the posterior teeth are protected in all excursions. Nevertheless, in other embodiments portions of the appliances can be disposed between some or all of the teeth.

The disclosed appliances can also help retrain the hyoid bone and supra/infra hyoid muscles by creating a reference position for a low lying tongue especially in patients with narrow dental arches and high palates. They can help balance an asymmetric hyoid bone. They help establish proprioception and stereognosis of the TMJ muscles and joints, and help tongue elevation and retraction and co-ordination of lingual muscles by retraining them. They may help the hyoid bone descend to its normal place approximately 5 mm+/−1 mm inferior to the incisor-dens axis (because of the consequent coordinated activity of lingual muscles as appliances are worn). The appliances help re-educate the swallow pattern. Attempting to modify the swallow reflex is a very difficult task. However, since the appliances achieve muscle harmony, attempting to modify the swallow reflex is easier. The appliances help neuromuscular re-education, mobilization and stabilization of the anterior, middle, and posterior parts of the tongue, and subsequently all the craniomandibular and craniocervical muscles. They thus help correct forward head posture. A tongue in an aberrant low posture can sit on top of the posterior mandibular teeth, thus preventing them from eruption in a growing child. When lower posterior teeth don't erupt, a low curve of Spee develops resulting in a reduced vertical dimension of growth of the orofacial complex. In an adult, low tongue posture creates several imbalances between external and internal forces of the oral environment and is the primary cause of bruxism and clenching creating a lot of force in the craniomandibular system. Retraining the tongue with the appliances balances the forces in an adult and allows proper growth and development in a child.

As the teeth erupt in the mouth, they are guided into a specific zone of neutrality that determines the horizontal position of each tooth in the arch. The perioral musculature in combination with the tongue, plays a profound role in determining a precise horizontal relationship of the anterior and posterior teeth. The devices disclosed herein can address neutral zone imbalances very effectively since they can address all the involved muscle groups, i.e. the buccinators, orbicularis oris, and all the muscles of the tongue.

The disclosed appliances can also allow a floating compression on the palate by the tongue to maintain the tensegrity for proper posture of the head, face, and neck. This can retrain the muscles of the tongue to facilitate proper muscles sequencing to correct mouth breathing and aberrant swallowing.

The human pharyngeal airway is a complicated structure comprising a number of muscles whose functional integration is essential for several complex tasks including swallowing, breathing, and speech. From the respiratory perspective, the primary goal of pharyngeal muscles is to keep the airway open allowing the flow of air. Since the appliance can be fluid filled, gel-filled, or solid with a flexibly-resilient material, suction of the tongue against the roof of the mouth can create an equalization of forces bilaterally. The appliances can harmonize activity of muscles of the soft palate such as the tensor veli paltini, levator veli palatine, musculas uvulae, palatoglossus, palatopharygeus, and the middle and inferior pharyngeal constrictor muscles, and once these muscles harmonize in function, it may help achieve a better velopharyngeal closure and maintain airway patency thus helping with sleep apnea.

None of the prior art appliances address the muscles and ligament attachments in the hamular notch-pterygoid plate-infratemporal area. The muscle/ligamentous attachments in this area can be very painful. The maxillary appliances described herein can sit on the hamular notch releasing pterygomandibular ligaments and lateral pterygoids because of their close proximity to the hamular notch. The connected tubes and pads (or bulges) in the buccal vestibule release the temporalis and masseter muscles bilaterally and the buccinators and orbicularis oris anteriorly. This may reduce pain and overload in the muscles and help patient sleep better because nociceptive pain input causing arousals is reduced.

Most prior art appliances do not address the cranial motion. These appliances described herein, because they encourage normal tongue position, have the potential to stimulate and sustain rhythmic cranial motion.

As far as bony structures, the fluid filled appliances can create osteopathic releases for cranial sutures such as the zygomatico-maxillary suture, cruciate sutures, sutures at the terminal end of the medial pterygoid plate of the sphenoid bone, midpalatine suture, anterior maxillary sutures etcetera.

The appliances, if worn prior to border molding and while establishing the vertical dimension of occlusion (VDO), can help deprogram and place all the supra and infra hyoid muscles, temporalis and masseter, buccinators and pharyngeal constrictor muscles in their physiologic state and thus muscles and VDO recording can be done in that position. The appliances can also aid in recording the tissues in a non-displaced position such as a physiological rest position.

The upper device addresses the upper and middle band of the buccinator-orbicularis oris complex and the lower device address the lower band of the same. The appliances can hence be used as myofunctional training appliances to encourage lip seal. The lip can be stretched over the anterior tubing in lip descent training to stretch the vestibular fibers of the upper or lower lips.

The appliances can also be used as a precursor for splint therapy whereby all the elements of stomatognathic system are in a state of bilateral harmony in rest and in function to achieve an organic occlusion, with coordinated activity of all muscles of the head, face and neck and thus record the physiologic position of the mandible in correcting neuromuscular dysfunction. This reproducible physiologic state of bilateral balance can be captured then for splint therapy for pivot splints, stabilization splints, or reduction splint.

As the tongue is trained to stay to the roof of the mouth, one can switch to lower volume appliances to gradually train proper tongue posture and eventually wean off the appliances. Thus, in some embodiments, a system of appliances can be included with varying sizes and shapes, such that the user can switch to smaller and smaller versions of the appliances.

The appliances can also be made from a semi-rigid material, which can be used to train a patient to do isometric contraction exercises to tighten the ligaments once joint congruency is achieved.

The upper appliance can also be used as a temporary obturator in cleft palate patients.

Figure 2:
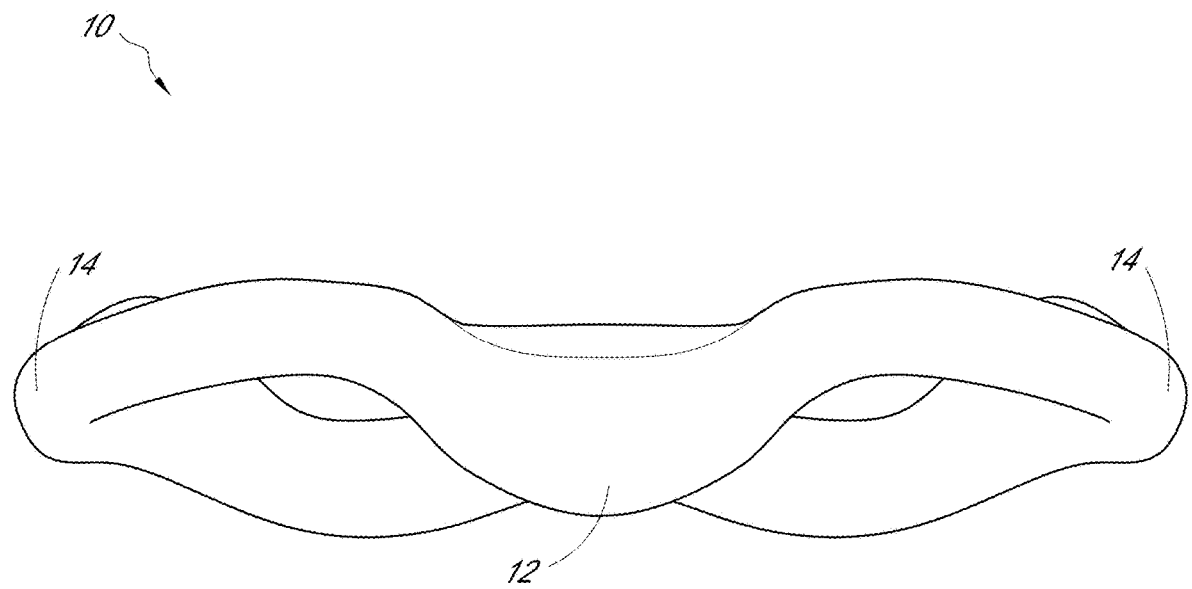
FIG. 2 is a rear view of the maxillary appliance of FIG. 1.
Figure 3:
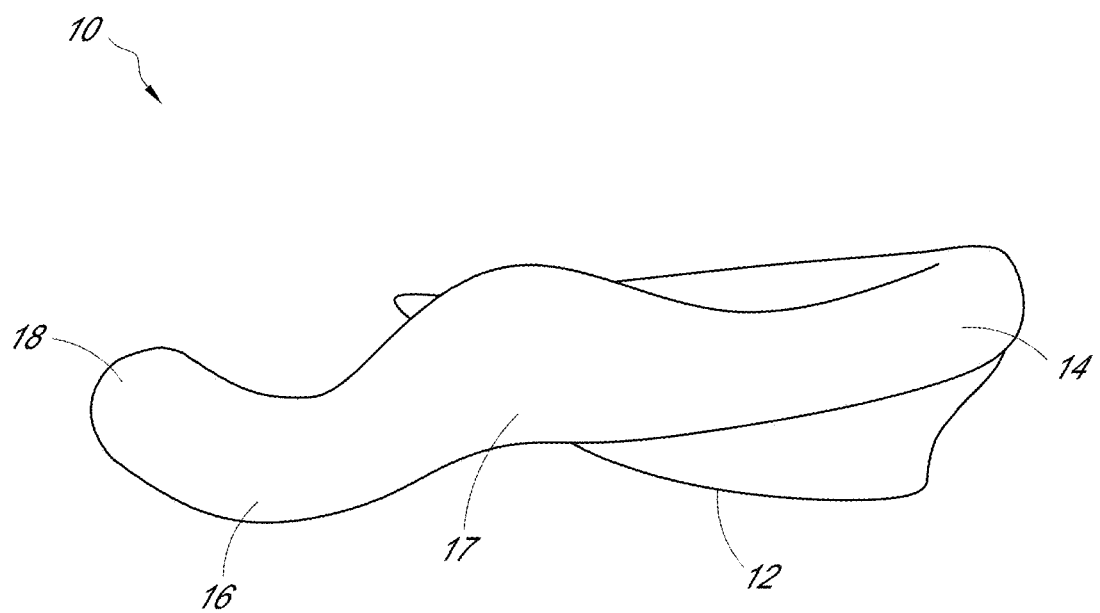
FIG. 3 is a side view of the maxillary appliance of FIG. 1.
Figure 4:
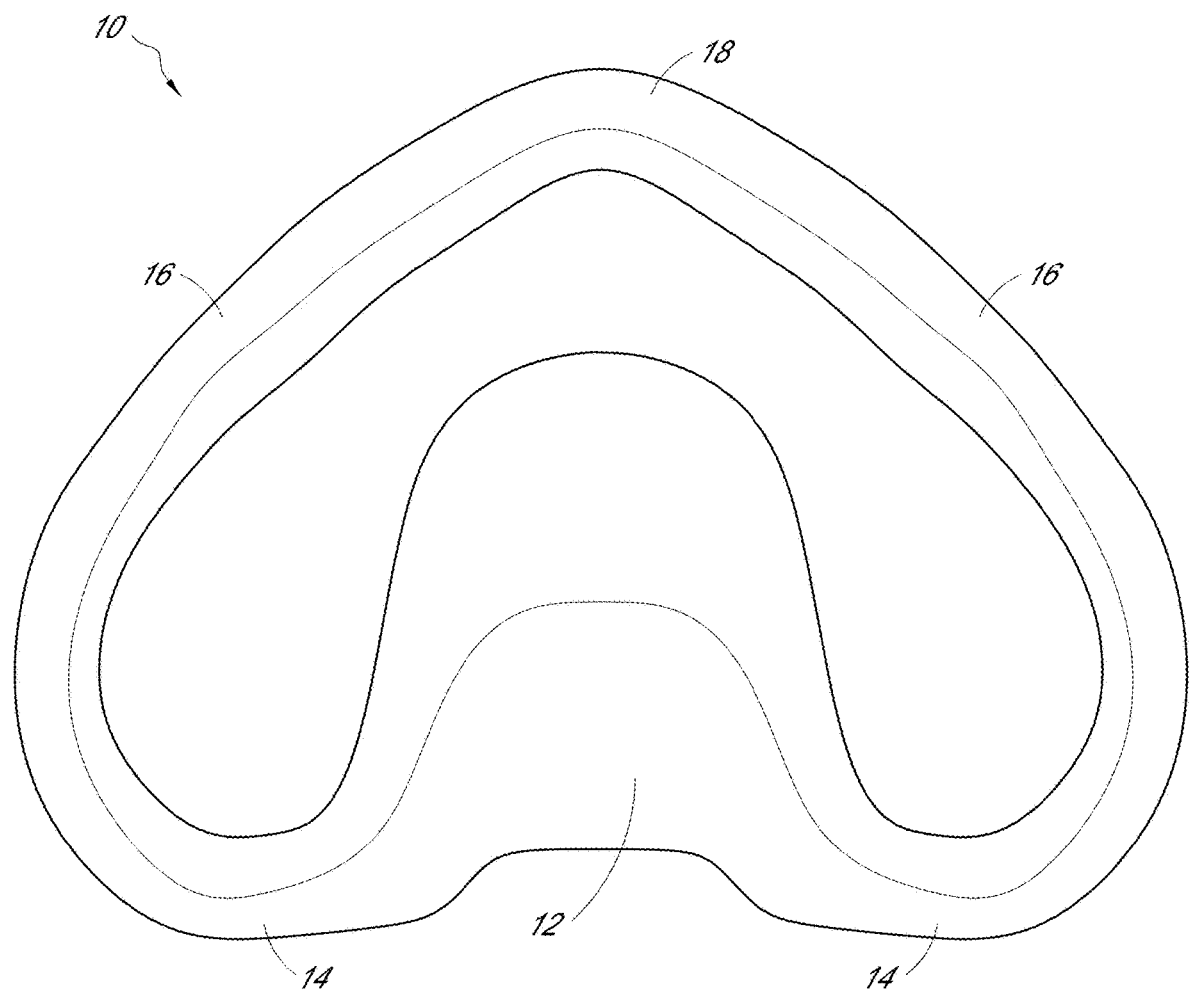
FIG. 4 is a top view of the maxillary appliance of FIG. 1.
Figure 5:
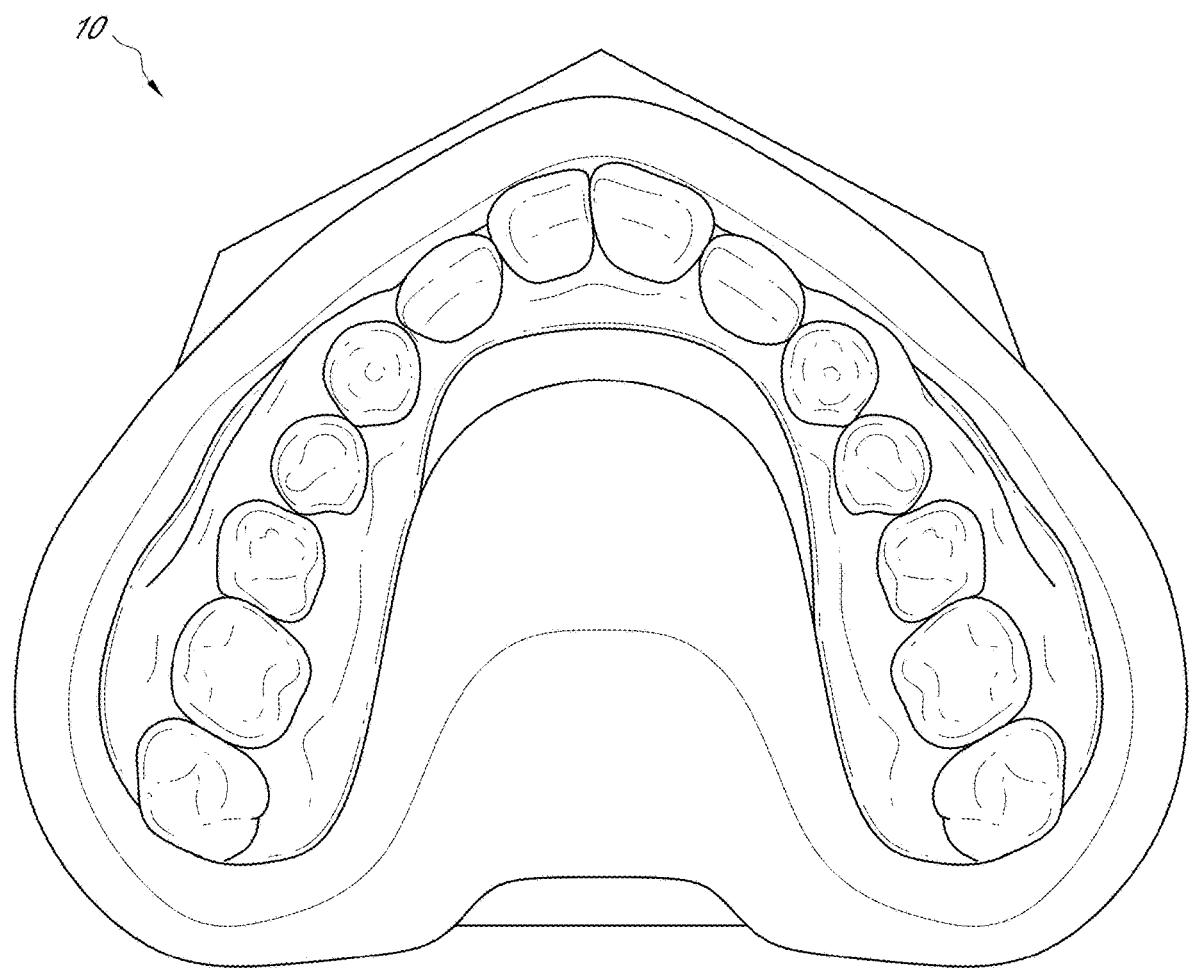
FIG. 5 depicts the maxillary appliance of FIG. 1 mounted to teeth.
Figure 6:
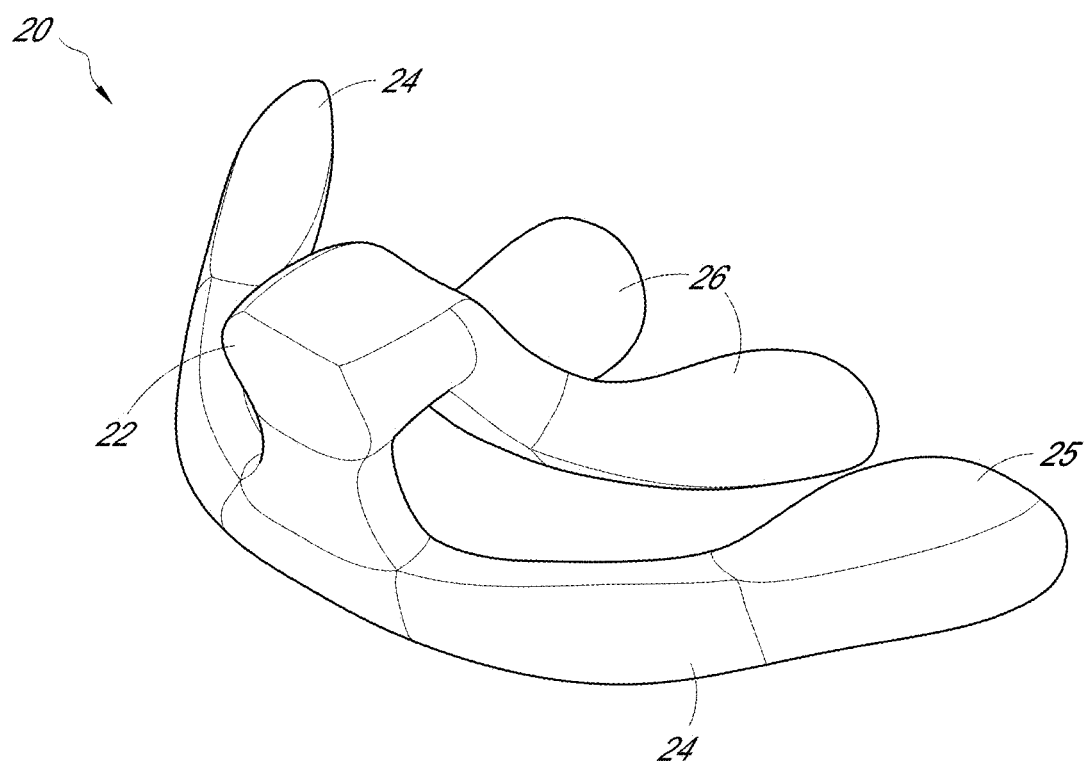
FIG. 6 is a perspective view of an embodiment mandibular appliance.
Figure 7:
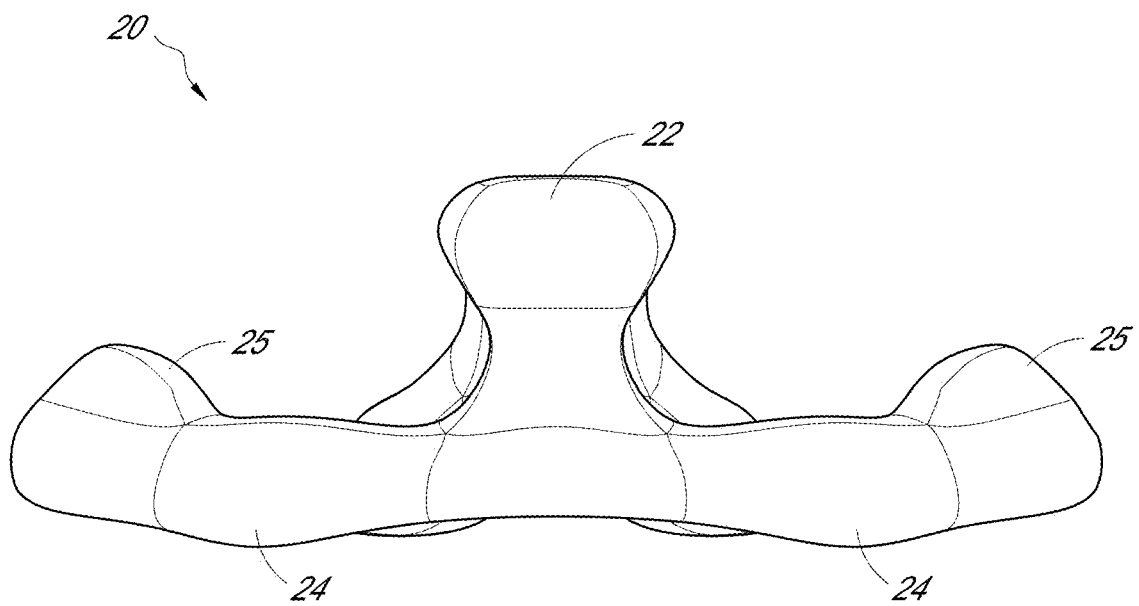
FIG. 7 is a front view of the mandibular appliance of FIG. 6.
Figure 8:
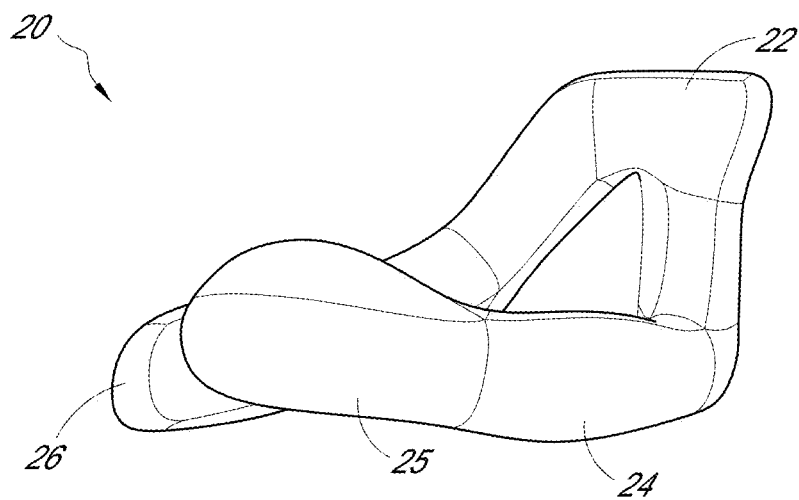
FIG. 8 is a side view of the mandibular appliance of FIG. 6.
Figure 9:
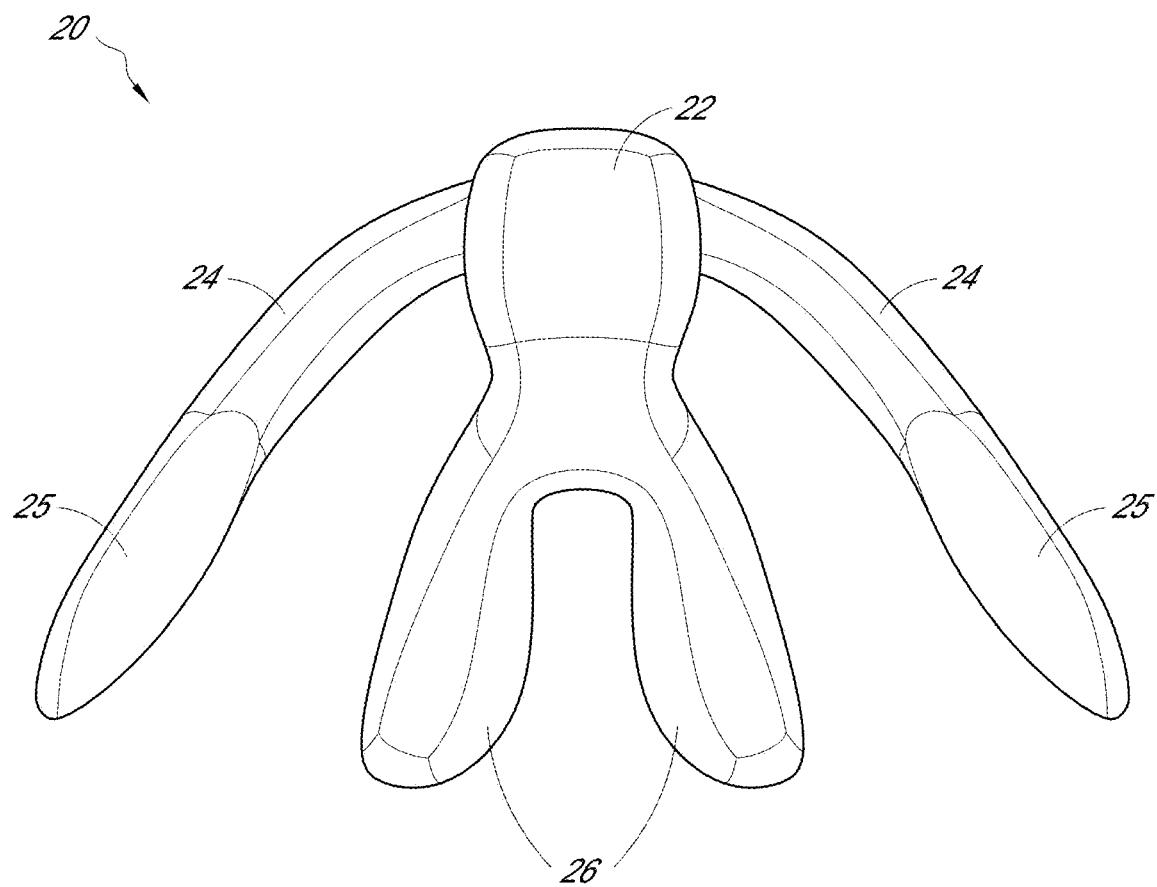
FIG. 9 is a top view of the mandibular appliance of FIG. 6.
Figure 10:
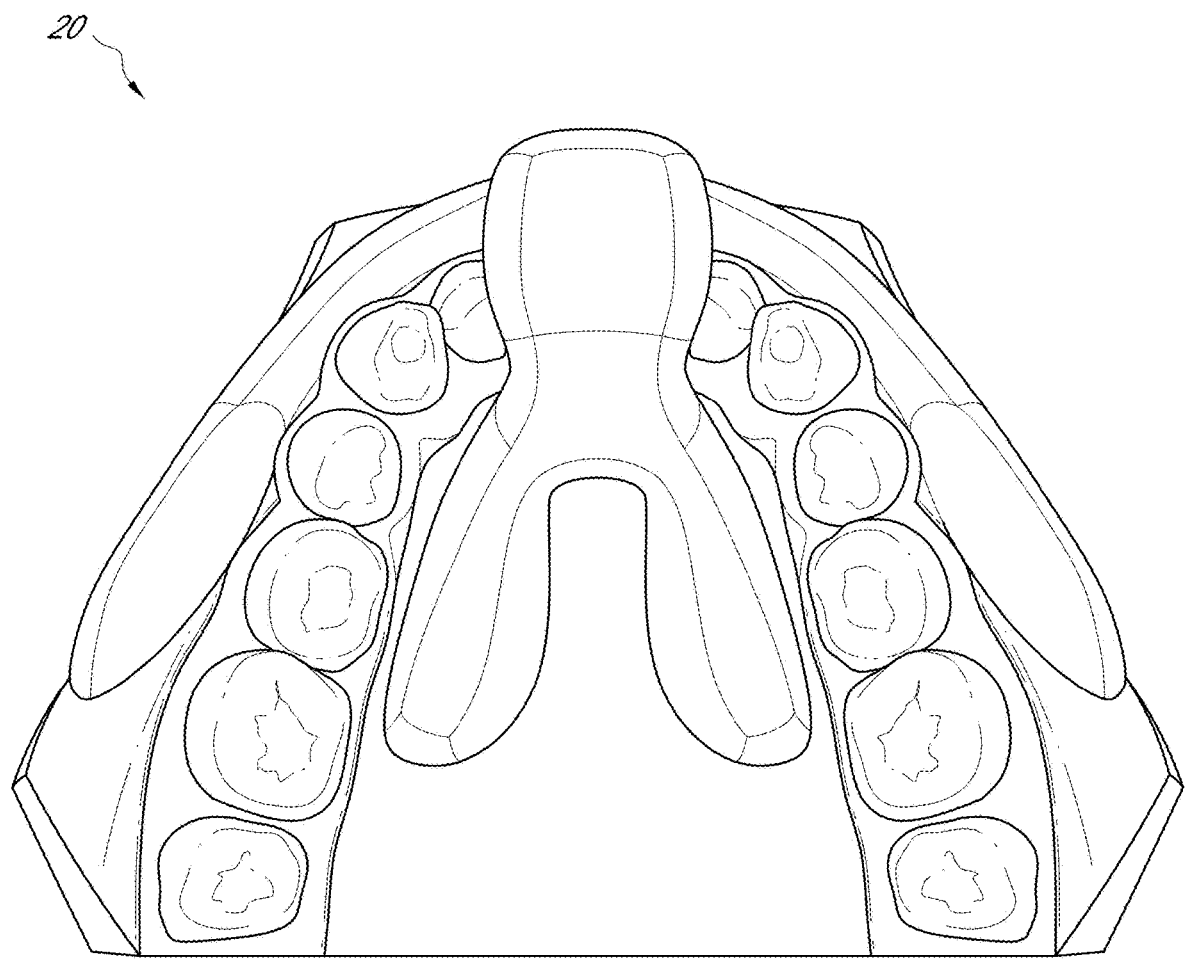
FIG. 10 depicts the mandibular appliance of FIG. 6 mounted to teeth.

As shown in the figures, two devices can be provided: a maxillary appliance 10 depicted in FIGS. 1-5 and a mandibular appliance 20 depicted in FIGS. 6-10. The maxillary appliance 10 can mount to the upper jaw, around the upper teeth in the area between the teeth, lips, and cheeks (such as the labial and buccal vestibule) and on the palate. The maxillary appliance 10 can include a tongue/palatal pad 12 against which the tongue can press. The palatal pad 12 can be mounted beneath the palate such that it can be contacted by a tongue moving upward toward the palate. The palatal pad 12 can further be located at a position high enough to allow a comfortable range of motion for the user's tongue, but still tending to be contacted by the user's tongue. The tongue pad can thus serve as a myofunctional trainer. It can train the tongue to stay at the roof of the mouth, with contact between the tongue and the pad 12 provoking a movement of the tongue upward toward the pad. This movement can allow muscles attached above and below the hyoid bone to assume their physiologic state of rest and activity.

The palatal pad 12 can also be substantially broad and continuous. For example, the pad 12 can optionally have a substantially continuous surface such that the tongue can form a continuous area of contact with the pad. The pad 12 can also optionally be substantially smooth, creating a comfortable surface for contact with the tongue. The pad 12 can also optionally be textured, colored, clear, or have designs printed thereon. The pad 12 can also optionally extend over substantially all of the palate between the upper teeth, or even further over substantially all of the palate. A palatal pad 12 that only covers the anterior portion of the palate will only provoke an upward motion of the anterior portion of the tongue. A palatal pad 12 that covers substantially all of the palate will provoke an upward motion of substantially all of the tongue. However, other variations of the palatal pad 12 are also possible. For example, in some embodiments the pad 12 can include one or more minimal holes that can allow for circulation of saliva or provide other functionality. Similarly, it may be desirable for the pad 12 to not cover substantially all of the palate, for example, when a user prefers a smaller device for comfort reasons.

The palatal pad 12 (and the entire appliance) can be formed from a variety of materials. In some embodiments, the palatal pad 12 can comprise a flexibly resilient material, configured to substantially retain its shape, but also to temporarily bend (while also providing some resistance) when a force is applied. This can allow the force from the tongue on the palatal pad 12 to be relatively balanced throughout the surface of contact between the tongue and the pad. However, the material can also be substantially rigid. In some embodiments, the pad can comprise a material such as polyvinyl chlorides; silicone or silicone rubbers; urethanes and polyurethanes; polyisoprenes; cyclic olefin copolymers, polymers, and polyolefins; thermoplastic elastomers; polyether block amides like Pebax, polyamides, or polyamide blends; polyethylenes; nylons or modified nylons; elastomers; thermoplastic vulcanizates like Santoprene; rubbers and modified rubbers; thermoplastic polyurethanes; thermoset rubber; acrylonite butadiene styrene (ABS); poly- carbonate (PC); PC/ABC blends; styrene; styrene foam; polypropelene, polyester etcetera. Further, in some embodiments the pad 12 can be fluid-filled, gel-filled, or fiber-filled, to further facilitate an even distribution of pressure. In some embodiments the palatal pad can include on or more minimal holes to allow for circulation of saliva or provide other functionality like delivery of salivary stimulants and medicaments. Other materials can also be used, such as a rigid material, and the pad 12 can also optionally be solid. The rest of the maxillary appliance 10 can also optionally be formed from any of these materials.

The maxillary appliance 10 can also include two hamular notch tubes 14. The hamular notch tubes 14 can connect to the palatal pad 12. They can be configured to mount around a maxillary tuberosity when the maxillary appliance 10 is mounted to a user's upper jaw. By mounting around the maxillary tuberosity, the hamular notch tubes 14 can allow the maxillary appliance 10 to have features on either side of the upper teeth, facilitating a secure mounting to the jaw. However, it should be noted that the depicted embodiment of the appliance does not contact the teeth, but instead contacts what is commonly-known as the gums (although contact with the teeth is also possible).

The hamular notch tubes 14 can also be positioned to address the buccinator muscles, the superior pharyngeal constrictor muscles, tensor veli palatine muscles, medial pterygoid and indirectly the lateral pterygoid because the hamular notch tube lies in close vicinity to the condylar head. To serve this function, it can be sufficient for the hamular notch tubes 14 to only contact the relevant tissue. However, in some embodiments it may also be desirable for the hamular notch tubes 14 to form a tight fit and thus apply pressure to the relevant tissue. The hamular notch tubes 14 can particularly be sized to fit in the hamular notch when the mouth is closed.

The maxillary appliance 10 can also include two buccal tubes 16, which can connect to each other and the hamular notch tubes 14 as shown in the figures. The buccal tubes 16 can extend along a user's upper and middle buccinators in the buccal vestibule and along the orbicularis oris in the labial vestibule. The buccal tubes 16 connecting to each other can, along with the hamular notch tubes 14 and the palatal pad 12, form a ring around the user's upper jaw and teeth.

The buccal tubes 16 can further include buccal bulges 17, which can be positioned substantially at the zygomatic arches to provide relief to the buccinators, masseter, and other adjacent maxillary muscles. Like the palatal pad 12, the buccal bulges 17 can be formed from a variety of materials and can be fluid-filled, gel-filled, fiber-filled, or solid.

The maxillary appliance 10 can also include a labial frenulum portion 18 along the buccal tubes 16, at a central anterior portion of the appliance. The labial frenulum portion 18 can form a space configured to receive the labial frenulum when the appliance is mounted to the upper jaw.

In further embodiments, the maxillary appliance can also optionally include a buccal flange extending vertically from the buccal tubes 16 and configured to protect the cheek (for example, if the appliance is worn during dental procedures). This can also provide relief to muscles during extended dental procedures when the user's mouth may become tired over time. A similar flange can also be provided on buccal tubes 24 of the mandibular appliance 20 (further described below). Similar devices may also include just a buccal flange and a hamular notch tube attached or detached from the appliance, which can provide similar protection and relief during dental procedures.

The mandibular appliance 20 can mount in the labial and buccal vestibule, on the floor of the mouth, and on the mandibular (lower) teeth and particularly to the incisor teeth. Like the maxillary appliance 10, the mandibular appliance 20 can also optionally be solid, fluid-filled, gel-filled, or fiber-filled (or use other materials), with strategically-designed tubes and pads (depicted as bulges). The mandibular appliance 20 can have two lingual lift pads 26 to support the tongue and lift and encourage the tongue to stay at the roof of the mouth. The lingual lift pads 26 can extend downwardly and inwardly from an anterior deprogrammer 22, but more generally can extend inwardly from the incisors when mounted to the lower teeth. However, in other embodiments the lift pads 26 can extend from other areas. The lift pads can be positioned to contact the tongue from beneath, further encouraging the tongue to lift upwards toward the palate (as also discussed above with reference to the maxillary appliance 10). The upper surface of the lift pads 26 can be sufficiently high to encourage the tongue upwards without uncomfortably limiting the tongue's range of motion. For example, this can be helpful for people who cannot tolerate anything on their palate because of inappropriate neurosequencing.

Further, as shown the lift pads 26 are described as two separate pads in a fork configuration. The fork configuration can provide room for a lingual frenulum to be received between the pads. This can be helpful in embodiments where the lift pads 26 are long enough to extend toward a posterior portion of the tongue. However, in other embodiments the lift pads 26 can be combined into a single lift pad, for example when the lift pad does not extend as far inward.

The lift pads 26 can also include bulges at their ends. These bulges can help provide relief to muscles at or near the base of the tongue.

The mandibular appliance 20 can also include an incisal pad that can be designed as an anterior deprogrammer 22. The anterior deprogrammer 22 can be designed to deprogram the temporalis and masseter muscles that exert excessive forces onto the jaw joints and craniomandibular complex from parafunctional activity or from faulty incisal guidance. This allows disclusion of the posterior teeth, thus facilitating an immediate relief from pain by shutting off almost ⅔rd of the muscle force. The anterior deprogrammer can be configured to cover a biting portion of one or more lower incisors when mounted to the user's lower teeth, such as the two central incisors. Other positions for the deprogrammer 22 are also possible. For example, in some embodiments the deprogrammer can be split into two separate portions covering the central and lateral incisors with a split in the middle to allow for individual sutural micro movements of the 2 halves of the mandible along the mandibular symphysis.

In alternative embodiments, the deprogrammer 22 can be included on the maxillary appliance 10. In such an embodiment, the maxillary appliance can optionally include or not include the hamular notch tubes 14, the buccal tubes 16, or the palatal pad 12. Similarly, the mandibular appliance 20 can optionally include a tube in the retromolar pad area, similar to the hamular notch tubes, and optionally also include a vertical extension that addresses the hamular notch area from the mandibular appliance. The mandibular appliance 20 can also optionally not include the deprogrammer or the buccal tubes 24 (further described below). In embodiments where the maxillary appliance 10 and the mandibular appliance 20 are provided together, the deprogrammer 22 can optionally be on either one of the two appliances, or on both.

The deprogrammer 22 can also optionally be adjustable. For example, in some embodiments the deprogrammer 22 can include a hinge, such that the angle of the upper surface can be adjusted. The hinge can optionally be located on an anterior side of the deprogrammer 22 on a mandibular appliance 20. Similarly, the hinge can optionally be located on a posterior side of a deprogrammer on a maxillary appliance or at the base of the pad in the center in either of a maxillary or mandibular appliance.

The height of the deprogrammer 22 can also be adjustable. For example, additional spacers can be added to the upper surface of the depicted deprogrammer 22 (or the lower surface of a maxillary deprogrammer). The additional spacers can come, for example, in sheets between 1 mm and 0.5 mm that can be glued or clipped onto the deprogrammer 22 or each other (such that multiple sheets can be applied). A system for treating musculoskeletal disorders and issues in the mouth and jaw can include the mandibular appliances described herein along with the spacers which can securely mount over the anterior deprogrammer to increase or decrease the height of the anterior deprogrammer.

The deprogrammer 22 can discourage excessive biting, as further discussed above. Placing the deprogrammer over anterior teeth can create a point of contact in the anterior portion of the mouth before any other portion of the mouth when biting. Typically, the anterior teeth apply less force than posterior teeth, so this can lead to a reduced bite pressure while the appliance is being worn. Similarly, as shown in the depicted embodiments, both of the appliances 10, 20 can optionally include nothing that covers the chewing surfaces of the other teeth (and particularly the molars, or the teeth posterior to the incisors). However, the appliances 10, 20 can also optionally include chewing pads over these portions of the teeth such as the molars and premolars.

The mandibular appliance 20 can also include buccal tubes 24 and buccal bulges 25 that can have the same set of properties available as are available for the buccal tubes 16 and bulges 17 on the maxillary appliance 10. As shown, the tubes 24 and bulges 25 on the mandibular appliance 20 can extend from a central anterior portion of the user's lower jaw (for example, from the anterior deprogrammer 22) rearwardly along the mandibular buccal vestibule, stopping before the end of the molar area. However, in other embodiments these buccal tubes 24 can be extended to the retromolar pad area, as discussed above. The buccal tubes and bulges 24, 25 can release muscle insertions of the mentalis, orbicularis oris, lower band of the buccinators and the pharyngeal constrictor muscles. The tubes and bulges can also coordinate and harmonize muscle activity in those areas. Since the tubes and bulges are connected, the appliance can equalize forces of muscle function, thus eliminating musculoskeletal and myofascial disharmony.

The maxillary and mandibular appliances 10, 20 can additionally include other features. For example, the appliances can optionally include a heating device, such as an electric heater configured to sooth adjacent muscles by providing heat to muscles adjacent the appliances 10, 20. The heater can also optionally be controlled, such that it can be activated by a remote device (for example, using a Bluetooth or other wireless signal), activated by an actuator on the device, or activated by a sensor on the device which can trigger the heater when desired. The heater can be located, for example, in the palatal pad 12 or the anterior deprogrammer 22, or any other area along the device and the materials of the appliances 10, 20 can optionally be configured to conduct heat from there to the other parts of the appliances.

The appliances 10, 20 can also optionally include vibrating devices, which can be controlled and located in ways similar to the heating device. The vibrating device can be configured to sooth adjacent muscles by massaging them, for example by vibrating at a soothing or healing frequency. The frequency can optionally be between 25 Hz and 150 Hz, such as the frequency of the "Cat Purr".

The appliances described herein can be mounted to a user's jaw and/or teeth. For example, a system for treating the various conditions discussed herein can include both a maxillary and a mandibular appliance, such that they can both simultaneously be mounted to the user's jaw. The system can also optionally include the appliances in different sizes. The appliances can optionally come in sufficient sizes and sufficiently flexible material, such that the devices do not need to be individually customized to fit most user's mouths. For example, in some embodiments the appliances can be pediatric and adult sizes. Further, the appliances can be sized such that a user can comfortably wear them continuously throughout the day, or alternatively overnight while sleeping, and this method of use can also be considered as part of the disclosure.

The appliances described herein can also optionally include various medicaments (for example, impregnated in the material or placed in the tubes when the appliances are hollow) such that they can be released slowly over time. The medicaments can be used to treat various symptoms in patients who have compromised swallow reflexes or can be designed to release salivary stimulants for users with dry mouth or burning mouth syndrome.

The various appliances, devices, methods, procedures, and techniques described above provide a number of ways to carry out the invention. Of course, it is to be understood that not necessarily all objectives or advantages described may be achieved in accordance with any particular embodiment described herein. For example, although the appliances can be used to treat the various musculoskeletal conditions described herein, they can also be used to treat other conditions or not treat some of the conditions listed herein. For example, in some embodiments the palatal pad can be removed, such that the tongue is not trained to move toward the palate. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. For example, in some embodiments various components of the appliances described herein can be provided modularly, such that each piece can be used with our without the others. In a more specific example, the palatal pad 12 may be detachable from the hamular notch tubes 14, such that the appliance can be modified to not include the palatal pad. Similarly, each component can then optionally be made of different materials, and then combined together. The modular attachments can also be made to isolate saliva to facilitate dental procedures if absorbent materials are used in a removable module. Or even a suction tube can be attached to it while the dentist is working in the patient's mouth. Accordingly, the invention is not intended to be limited by the specific disclosures of preferred embodiments herein.

What is claimed is:

1. A mandibular appliance configured to be mounted to a user's lower jaw and teeth, the mandibular appliance comprising:
    two buccal tubes extending from a central anterior portion of the user's lower jaw rearwardly along opposite mandibular buccinators when mounted to the user's lower jaw, the two buccal tubes structured to be positioned only in the labial and buccal vestibules adjacent to the user's mandibular teeth when mounted to the user's lower jaw and not cover a chewing surface of the user's molars when mounted to the user's lower jaw;
    an anterior deprogrammer, connected to the two buccal tubes and configured to cover a biting portion of one or more lower incisors when mounted to the user's lower teeth; and
    a lingual lift pad extending inwardly and downward from the anterior deprogrammer, comprising a fork configuration where two ends of the lingual lift pad are long enough to extend toward a posterior portion of the tongue and defining a gap therebetween, the gap being configured to receive a lingual frenulum when the mandibular appliance is mounted to the user's lower jaw and teeth, and wherein the lingual lift pad is configured to be positioned beneath the tongue such that a lower surface of the lingual lift pad rests on the floor of the user's mouth and an upper surface of the lingual lift pad contacts the ventral surface of the tongue and lifts the tongue upward toward the roof of the mouth when the mandibular appliance is mounted to the user's lower jaw and teeth.

2. The mandibular appliance of claim 1, wherein the anterior deprogrammer comprises a hinge such that an angle of an upper surface of the anterior deprogrammer can be adjusted.

3. The mandibular appliance of claim 1, wherein the two buccal tubes comprise bulges adapted to be placed on the lower molar area.

4. The mandibular appliance of claim 3, wherein the bulges are fluid-filled.

5. The mandibular appliance of claim 3, wherein the bulges are gel-filled.

6. The mandibular appliance of claim 3, wherein the bulges are fiber filled.

7. The mandibular appliance of claim 3, wherein the bulges are medicament filled.

8. The mandibular appliance of any one of claims 1 and 2-7, wherein the mandibular appliance is configured to not cover a chewing surface of a user's molars when mounted in a user's lower jaw and teeth.

9. The mandibular appliance of any one of claims 1, and 2-7, further comprising a heater mounted within the mandibular appliance.

10. The mandibular appliance of any one of claims 1, 2-7, further comprising a motor configured to vibrate the mandibular appliance at a muscle-soothing or healing frequency.

11. The mandibular appliance of claim 10, wherein the muscle-soothing or healing frequency is between 25 Hz and 150 Hz.

12. A method comprising:
    providing a mandibular appliance having
        two buccal tubes extending from a central anterior portion of the user's lower jaw rearwardly along opposite mandibular buccinators when mounted to the user's lower jaw, the two buccal tubes structured to be positioned only in the labial and buccal vestibule adjacent to the user's mandibular teeth and not cover a chewing surface of the user's molars when mounted to the user's lower jaw;

an anterior deprogrammer, connected to the two buccal tubes and configured to cover a biting portion of one or more lower incisors when mounted to the user's lower teeth, and a lingual lift pad extending inwardly and downward from the anterior deprogrammer, comprising a fork configuration where two ends of the lingual lift pad are long enough to extend toward a posterior portion of the tongue and defining a gap therebetween, the gap being configured to receive a lingual frenulum when the mandibular appliance is mounted to the user's lower jaw and teeth, and wherein the lingual lift pad is configured to be positioned beneath the tongue such that a lower surface of the lingual lift pad rests on the floor of the user's mouth and an upper surface of the lingual lift pad contacts the ventral surface of the tongue and lifts the tongue upward toward the roof of the mouth when the mandibular appliance is mounted to the user's lower jaw and teeth, mounting the mandibular appliance to the user's lower jaw and teeth for treating musculoskeletal disorders and issues in user's mouth and jaw joints.

13. The method of claim 12, further comprising adjusting an angle of an upper surface of the anterior deprogrammer.

14. The method of any one of claims 12 and 13, further comprising vibrating the mandibular appliance while mounted to a user's lower jaw and teeth.

15. The mandibular appliance of claim 1, wherein the mandibular appliance comprises a material impregnated with a medicament.

16. The mandibular appliance of claim 1, further comprising a medicament in the mandibular appliance.

17. The mandibular appliance of claim 1, wherein the mandibular appliance is hollow and comprises a medicament in the mandibular appliance.

18. The mandibular appliance of claim 1, wherein the two buccal tubes are hollow and have a medicament therein.

19. The method of claim 12, wherein the mandibular appliance comprises a material impregnated with a medicament, and the method further comprises releasing the medicament to the user's mouth over time.

20. The method of claim 12, wherein the mandibular appliance is hollow and comprises a medicament in the mandibular appliance, and the method further comprises releasing the medicament to the user's mouth over time.

21. The method of claim 12, wherein the two buccal tubes of the mandibular appliance contain a medicament, and the method further comprises releasing the medicament to the user's mouth over time.

* * * * *

UNITED STATES PATENT AND TRADEMARK OFFICE
CERTIFICATE OF CORRECTION

| | |
|---|---|
| PATENT NO. | : 11,737,910 B2 |
| APPLICATION NO. | : 16/137335 |
| DATED | : August 29, 2023 |
| INVENTOR(S) | : Mamta Ketan Shah |

It is certified that error appears in the above-identified patent and that said Letters Patent is hereby corrected as shown below:

In the Specification

Column 14, Line 52, In Claim 9, delete "2-7," and insert -- 2-8, --.

Signed and Sealed this
Twenty-eighth Day of November, 2023

*Katherine Kelly Vidal*

Katherine Kelly Vidal
*Director of the United States Patent and Trademark Office*